(12) United States Patent
Schwind et al.

(10) Patent No.: US 6,203,706 B1
(45) Date of Patent: *Mar. 20, 2001

(54) SYNTHETIC PARTICLES AS AGGLUTINATION REAGENTS

(75) Inventors: Peter Schwind, Fribourg (CH); David Bashforth, Neuchatel (GB); Roderick N. Hobbs, Chester (GB); Graham Margetts, Shrewsbury (GB); Michael J. Marshall, Oswestry (GB); Mark J. J. Roberts, Shrewsbury (GB)

(73) Assignee: Stiftung fur Diagnostische Furschung, Morat (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/991,883

(22) Filed: Dec. 16, 1997

(30) Foreign Application Priority Data

Dec. 18, 1996 (EP) ................................. 96 120 421

(51) Int. Cl.[7] ................................................. G01N 33/544
(52) U.S. Cl. .......................... 210/645; 210/782; 530/815; 436/528; 436/823
(58) Field of Search .................................. 210/782, 645, 210/787; 530/813, 815; 435/2; 422/56, 57; 436/528, 531, 177, 823

(56) References Cited

U.S. PATENT DOCUMENTS

| | | | |
|---|---|---|---|
| 4,021,534 | | 5/1977 | Lafontaine . |
| 4,321,058 | * | 3/1982 | Tomiyama et al. . |
| 4,397,960 | * | 8/1983 | Moussebois et al. . |
| 4,559,303 | * | 12/1985 | Aotani et al. . |
| 4,605,686 | * | 8/1986 | Obana . |
| 4,659,658 | * | 4/1987 | McCarthy et al. . |
| 4,711,841 | * | 12/1987 | Kronvall . |
| 4,829,011 | * | 5/1989 | Gibbons . |
| 4,891,324 | * | 1/1990 | Pease et al. . |
| 5,405,784 | * | 4/1995 | Van Hoegaerden . |
| 5,512,432 | * | 4/1996 | Lapierre et al. . |
| 5,552,064 | | 9/1996 | Chachowski et al. . |
| 5,665,558 | * | 9/1997 | Frame et al. . |

FOREIGN PATENT DOCUMENTS

| | | |
|---|---|---|
| 0 158 443 | 10/1985 | (EP) . |
| 0 279 525 | 8/1988 | (EP) . |
| 0 305 337 | 8/1988 | (EP) . |
| 0 348 174 | 12/1989 | (EP) . |

* cited by examiner

Primary Examiner—Matthew O. Savage
Assistant Examiner—Terry K. Cecil
(74) Attorney, Agent, or Firm—Arent Fox Kintner Plotkin Kahn

(57) ABSTRACT

Described is a method and reagent kit for the detection of an analyte in a sample liquid by agglutination, wherein the sample liquid is contacted with an agglutination reagent in a reaction vessel that contains an inert matrix to form a reaction mixture that is then subjected to centrifugation. The reaction between the analyte and the agglutination reagent is determined based upon the penetration of the agglutination reagent into the inert matrix. The agglutination reagent includes synthetic particles having an average diameter and specific density chosen such that the particles' sedimentation behavior towards the matrix is essentially the same as that of erythrocytes under the same centrifugal conditions. Preferably, the surfaces of the synthetic particles have ligand molecules immobilized thereon for binding to the analyte.

26 Claims, 5 Drawing Sheets

TEST PROCEDURE, SCHEMATIC

Fig.1: 1-3 POSITIVE REACTIONS OF DECREASING STRENGTH
4 NEGATIVE REACTION

Fig.2: TEST PROCEDURE, SCHEMATIC

Fig.3: REACTIONS IN THE REACTION CHAMBER AND IN THE BUFFER SUPERNATANT OR IN THE GEL MATRIX IF THIS CONTAINS ANY-IgG ANTIBODIES

Fig.4: DIFFERENTIAL DIAGNOSIS OF 2 DIFFERENT ANALYTES A1 (RED PARTICLES) AND A2 (BLUE PARTICLES) IN ONE REACTION VESSEL; A) A1-POS./A2-NEG; B) A2-POS./A1-NEG; C) A1-POS./A-2POS; D) A1-NEG./A2-NEG.

Fig.5: DEFINITION OF THE SEDIMENTATION ZONES IN TABLES 1 AND 2

SYNTHETIC PARTICLES AS AGGLUTINATION REAGENTS

DESCRIPTION

The present invention concerns a method for the detection of an analyte in a sample liquid by agglutination wherein the sample liquid is contacted with an agglutination reagent and an inert matrix, the reaction mixture is subjected to the action of gravitation and the reaction between the analyte and the agglutination reagent is determined. Furthermore new reagents are disclosed for carrying out the method according to the invention.

Methods for the detection of analytes by haemagglutination and particle agglutination tests are known. These tests are used above all to detect antigens and antibodies for the diagnosis of infectious diseases. However, a common disadvantage of all these methods is that they are time consuming and labour-intensive and that the results are often very difficult to interpret.

Gel immunoassay methods in which haemagglutinates are separated from individual non-agglutinated erythrocytes by a centrifugation step through an inert matrix (cf e.g. EP-A-0 194 212, EP-A-0 305 337, EP-A-0 557 546, EP-A-0 634 216, EP-A-0 485 228 and WO 95/31731) are known for haemagglutination tests in which unfixed erythrocytes are used as agglutination reagents. In these methods agglutinated erythrocytes are retained on or in the inert matrix and can thus be distinctly separated from non-reacting single erythrocytes which can penetrate through the matrix and sediment to the bottom of the reaction vessel.

Only in EP-A-0 305 337 which goes back to a priority application from the year 1987 is there a statement that synthetic particles such as latex or polymerized agarose can also be used as agglutination reagents. However, there is no information about the properties of such synthetic particles. Furthermore this proposal was not taken up in the following period either in patents or in other publications. On the contrary recent publications such as EP-A-0 557 546 emphasise unfixed erythrocytes as agglutination reagents.

However, a disadvantage of unfixed erythrocytes is their instability which, under certain reaction conditions, leads to haemolysis. This instability often results in undesirably short expiry dates of products based on unfixed erythrocytes. Moreover a standardized and reproducible production of erythrocyte preparations, in particular of antibody-coupled or antigen-coupled erythrocyte preparations, can only be achieved in a very labour-intensive manner. This practically rules out an adequate uniformity of the physical properties of erythrocyte preparations.

Hence an object of the present invention was to at least partially eliminate the aforementioned disadvantages which result from the use of erythrocytes as agglutination reagents. In particular the present invention intends to provide synthetic particles which can be used as agglutination reagents and are capable of simulating the behaviour of erythrocytes in known gel immunoassays. Furthermore the synthetic particles should allow a simple coupling of biological substances and should be structured so as to be at least equivalent agglutination reagents to the previously used erythrocytes with regard to sensitivity and specificity. It should be possible to use these synthetic particles in agglutination methods that are easier to carry out and evaluate than the previously known methods.

This object is achieved by a method for the detection of an analyte in a sample liquid by agglutination, wherein the sample liquid is contacted with an agglutination reagent and an inert matrix, the reaction mixture is subjected to the influence of gravitation and the reaction between the analyte and the agglutination reagent is determined, characterized in that synthetic particles are used as the agglutination reagent whose diameter and density are selected such that their behaviour towards the matrix is essentially the same as that of erythrocytes.

It was surprisingly found that, if both the density and the diameter are optimally adjusted, synthetic particles can in fact be produced which can pass through an inert matrix without difficulties in a gel immunoassay and hence perfectly simulate fresh erythrocytes.

In the experiments that led up to the present invention it was observed that there was a greater delay in the passage of rigid polymer particles compared to erythrocytes (diameter 6–8 $\mu$m). Under given standard conditions this meant specifically that commercially available standard particles with a diameter of 3–7.5 $\mu$m only sediment incompletely in the gel matrix whereas larger (11.9 $\mu$m) or smaller synthetic particles (<1 $\mu$m) are only able to penetrate slightly into the gel. Although an increase in the parameters centrifugation period (from 10 min up to 50 min) and centrifugation speed (from 1030 to 1300 rpm) improved the sedimentation it was still not complete. Even if both these measures would have been able to achieve an optimal sedimentation, a change/increase in the centrifugation period and speed is, however, very disadvantageous for the following reasons:

1. The system according to the invention should allow a particularly non-time-consuming procedure relative to comparable methods. Thus a possible centrifugation period of 50 min would have tripled the intended test period of 20 min including incubation.
2. As is well known to a person skilled in the art the sensitivity in the gel centrifugation method decreases with increasing centrifugation speeds.
3. If the specified parameters can be adhered to, a commercially available centrifuge would be available for the system according to the invention.

It was surprisingly found that during passage through the inert matrix a comparable behaviour to erythrocytes can be achieved with synthetic particles of a smaller diameter than that of erythrocytes and a higher density than usual. In this connection it is possible to use spherical as well as asymmetric synthetic particles.

Synthetic particles with an average diameter of $\leq 5$ $\mu$m and in particular of 1 to 5 $\mu$m have proven to be preferable for the method according to the invention. The average diameter is particularly preferably between 2 and 4 $\mu$m. The specific density of the particles is preferably $\geq 1.1$ and is more favourably in the range of 1.1 to 1.8. The specific density is preferably in the range of 1.1 to 1.6 and most preferably in the range of 1.15 to 1.4 especially when the detection method is carried out under standard conditions as defined for known commercial erythrocyte gel immunoassays (e.g. DiaMed).

The synthetic particles used as an agglutination reagent in the method according to the invention are preferably organic polymer or copolymer particles. Particularly preferred materials are styrene and styrene derivatives such as bromostyrenes and in particular copolymers thereof. The manufacture of uniform polymer particles in a size range suitable for the agglutination reagents according to the invention is adequately well-known to a person skilled in the art (Arshady (1992): Suspension, emulsion and dispersion polymerization: A methodological Survey. Colloid & Polymer Science 270, 717–732; Okubo and Shiozaki (1992): Production of micron-size monodisperse polymer particles by seeded polymerization utilizing dynamic swelling method with cooling process. Polymer International 30, 469–474). Such methods usually utilize a combination of emulsion and dispersion polymerization in order to produce particles with exactly defined physical properties.

For the visual detection of the agglutination reaction in the method according to the invention it is possible to incorporate dyes, in particular water-insoluble dyes, into the particles. Thus synthetic particles dyed blue, yellow, green, black or red have proven to be particularly well suited for a visual evaluation. In a particularly preferred embodiment of the present invention red particles are used due to their especially good detectability.

The robustness of the synthetic particles enables a large number of different ligands to be immobilized on their surface by known standard industrial methods. In this process it is expedient to immobilise ligand molecules which are capable of binding to the analyte to be determined. The ligand molecules can be immobilized by adsorptive, covalent or high affinity interactions. The covalent coupling can for example be achieved by chemically reactive groups that are exposed on the surface. Examples of such groups are carboxyl, amino, aldehyde and epoxy groups. Immobilization by means of high affinity interactions is mediated by two partners of a high affinity binding pair such as streptavidin or avidin/biotin, hapten/antibody, saccharide/lectin etc. These covalent and high affinity interactions enable the immobilization of ligand molecules such as peptides e.g. peptides prepared synthetically, proteins e.g. glycoproteins, lipoproteins, recombinant polypeptides, immunoglobulins, nucleic acids e.g. DNA or RNA, nucleic acid analogues, saccharides e.g. monosaccharides, disaccharides, oligosaccharides and polysaccharides, lipids, hormones, metabolites or other biological substances. In this connection the immobilization can be achieved directly or by using linkers in order to achieve in a controlled manner a preferred optimal orientation of the bound ligand molecules.

It is, however, also possible to immobilise ligand molecules by purely adsorptive processes. This is for example possible for cell membranes such as membranes of erythrocytes, thrombocytes or leucocytes, fragments of cell membranes or lysates of cells or pathogens such as viruses, bacteria or parasites. If dyed synthetic particles are used it is not necessary to additionally dye the membranes.

The method according to the invention concerns the detection of an analyte in a sample liquid. Body fluids preferably serve as the sample liquid which can be optionally diluted such as blood, serum, plasma, saliva or urine. The volume of the sample liquid for the method according to the invention can be varied over wide ranges, volumes of 1 to 200 $\mu$l are preferably used for microtests.

The described synthetic particles are used as an agglutination reagent in the method according to the invention. The surface of these particles preferably contains a specific ligand molecule that is capable of binding with high affinity to the analyte. The agglutination reagent usually contains several binding sites for the analyte which enables the formation of cross-linked agglutination complexes composed of analyte and agglutination reagent.

The analytes that can be detected by the method according to the invention are substances which can interact specifically and with high affinity with the agglutination reagent e.g. antigens and antibodies that can be determined by an immune reaction and also nucleic acids which can be determined by a hybridization reaction. A first preferred embodiment of the present invention concerns the detection of antibodies as analytes in the sample liquid e.g. antibodies to pathogens such as viruses (HIV, hepatitis viruses), bacteria or protozoa, antibodies to autoantigens, antibodies to tumours or antibodies to allergens.

Furthermore the method according to the invention also enables a class-specific detection of antibodies e.g. a differentiation between IgG and IgM antibodies which is often of considerable importance for the diagnosis of for example infectious diseases and autoimmune diseases.

On the other hand antigens can also be determined by the method according to the invention e.g. free antigens such as serum proteins, metabolites, hormones, mediators etc. or carrier-bound antigens such as cellular blood group antigens.

In the method according to the invention a reaction vessel containing a matrix is used so that after the action of gravitational forces it is possible to qualitatively or semi-quantitatively determine the agglutination reaction between the analyte to be determined and the agglutination reagent. Although the action of gravitational forces can also be achieved by a relatively long sedimentation, it is preferable to use a centrifugation since the desired sedimentation can already be achieved after a short time. The optimal conditions with regard to the centrifugation period and g number can be easily determined by a person skilled in the art for any analytical system. These conditions are in particular determined by the nature of the agglutination complex between agglutination reagent and analyte, the components of the reaction mixture in the unbound state as well as the matrix used in each case. An inert particulate matrix is preferably used in the method according to the invention. On the other hand it is also for example possible to use the compact matrix described in EP 96 10 428.3.

The matrix is preferably an inert particulate matrix. The "inert" characteristic emphasises the fact that the matrix should not react unspecifically with the analyte or the agglutination reagent. Particles that are commercially available for liquid chromatography (e.g. from Merck, Pharmacia, Bio-Rad, Tosohaas) are preferably used as the matrix. Specific examples are Sephadex®, Sepharose®, Sephacryl®, Bio-Gel® or Toyopearl®. These are products based on cross-linked polymers or copolymers such as agarose, polyacrylamide, polydextran, styrene/divinylbenzene or polymethacrylate. Glass beads also come into consideration. The grain sizes of the particles of the matrix are preferably 10 $\mu$m to 200 $\mu$m. Matrices also come into consideration to which detection reagents such as antibodies are already coupled such as those which are obtainable from the Pierce or Pharmacia Companies. A person skilled in the art can determine with simple preliminary experiments whether particles can be used for a particular detection method.

The results of the method according to the invention are interpreted such that after the action of gravitational forces on the reaction mixture
a) the reaction product composed of the analyte to be determined and the agglutination reagent cannot penetrate into the matrix or only to a slight extent when there is a strong agglutination,
b) the reaction product enters the matrix but cannot completely penetrate it when there is a weak agglutination and
c) the particles present in the reaction vessel can essentially completely penetrate the matrix when there is no agglutination.

In a preferred embodiment of the method according to the invention two or several different types of synthetic particles are used as agglutination reagents. There are namely various diseases that are associated with one another in which a so-called screening has to be firstly carried out with conventional test methods to establish whether the examined person has antibodies to a disease belonging to this group. If the tested body fluid of the examined person is positive in the screening test, then, according to conventional methods, it has to be subjected in a second step to a so-called differentiation test in which it is then determined towards which of the diseases in the group the antibodies are directed. A typical example of this type of procedure is HIV diagnostics. In the screening it is determined whether HIV-specific antibodies are present. The differentiation determines whether these are directed towards HIV-I, towards HIV-II or HIV-I and HIV-II.

In the method according to the invention it is now possible to use two different types of synthetic particle which preferably do not differ in size, form, density and flexibility but have a different colouring e.g. red and blue and are differently equipped with surface ligands. Since a homogeneous suspension is formed from these different species of synthetic particles which has the same proportions of each species, this suspension can be used in the same way as for a single test. The results can then be interpreted as follows: If both analytes to be determined are present in the sample liquid, this results in a red and a blue band on the matrix or in the upper region after centrifugation. If only one analyte is present, one band of the appropriate colour can be detected in the upper region of the matrix whereas the synthetic particles of the other colour penetrate through the matrix and are located below it. If neither the first nor the second analyte are present in the sample liquid, a layer of both synthetic particles forms below the matrix. correspondingly it is of course also possible to use three or more different synthetic particles with different colours in order to simultaneously differentiate between the corresponding number of parameters.

Any reaction vessels that are suitable for use in a gel agglutination test can be used to carry out the method. The volume of the reaction vessels is preferably 50 µl to 2 ml. The reaction vessels are preferably equipped with a funnel to receive the reagents. In a preferred embodiment an arrangement of several reaction vessels is used which are arranged together on a card or disk. These reaction vessels located on a card or disk can either be designed to detect the same analyte or to detect different analytes.

For example the cards sold by the DiaMed Company for blood group analysis on which six microreaction vessels are arranged can be used to carry out the method according to the invention. It is also possible to use products from the Ortho and Diagast Companies.

The action of gravitation on the reaction mixture preferably takes place by centrifuging the reaction vessels in a suitable centrifuge. Thus in a preferred embodiment of the method according to the invention the commercially available DiaMed ID centrifuge 12 S II with the preset parameters (t=10 min, v=85 g) is used.

In a further preferred embodiment of the present invention it is, however, also possible to use modified centrifugation methods which especially take into account the kinetics of the underlying reactions. This is reflected in a reaction amplification of weak reactions in particular.

Furthermore for certain embodiments of the method according to the invention it is preferable to use matrices that contain a second antibody, for example a so-called group-specific antibody such as anti-IgG. In this case a two-phase reaction takes place in the reaction vessels. The first reaction takes place in the reaction chamber if, in the case of a positive reaction, the ligand molecule on the synthetic particles e.g. an antigen reacts with the analyte in the sample e.g. an antigen-specific antibody. In this case cross-linking between the various synthetic particles (agglutination) can already occur which, however, in the case of IgG reactions often only leads to very weak agglutinates. The second antibodies present in the matrix ensure the desired effect of a specific reaction amplification by an additional cross-linking between already formed agglutination complexes.

With a total test period of only 20 min. the described test system according to the invention allows a significant saving of time compared to known systems. In comparison to test systems which are based on fixed or unfixed erythrocytes as an agglutination reagent there is an additional advantage of the much longer shelf-life of the synthetic particles as well as of the improved uniformity of the starting material.

If the test system is prepared appropriately the procedure is simple and the results can be read unequivocally so that the test can also be carried out by medical ancillary staff. The application is very simple since it only comprises two pipetting steps. Moreover with a centrifuge and a vortex instrument powered by an battery the determinations can easily be carried out outside permanent laboratory facilities without a power connection. The small amount of sample, the absence of washing steps as well as the possibility of sealing the reaction vessels after use ensures the shortest possible exposure of personnel to potentially infectious material and the best possible control of potentially infectious waste.

The present invention in addition concerns synthetic particles with an average diameter of $\leq 5$ µm, preferably of 1–5 µm, especially preferably of 2–4 µm and a specific density $\geq 1.1$, preferably of 1.1–1.8, particularly preferably of 1.15–1.4 on the surface of which ligand molecules are immobilized by for example covalent, adsorptive or high-affinity interactions. The particles are preferably dyed. These particles can be used as agglutination reagents in an agglutination test preferably in a gel agglutination test.

Yet a further subject matter of the present invention is a reagent kit for the detection of an analyte in a sample liquid comprising a) at least one reaction vessel which contains an inert matrix and preferably a particulate matrix and b) at least one type of synthetic particles on the surface of which ligand molecules are immobilized.

In certain types of the method of determination according to the invention it is preferable to add a detergent to the reaction mixture. Examples of suitable detergents are ionic detergents such as SDS, or non-ionic detergents such as Triton X-100 and Tween 20. Furthermore it may also be preferable to add mucins. The addition of detergents or/and mucins can improve the uniformity of the particles in the suspension or during the gel passage. This leads to a more complete sedimentation when there is a negative reaction.

It may also be expedient to carry out the reaction with the addition of a reducing agent e.g. a sulfhydryl reagent such as 2-mercapto-ethanol, dithiothreitol or sodium dithionite or another reducing agent such as tributyl phosphine. Reducing agents can reduce unspecific reactions such as those caused for example by IgM antibodies.

Furthermore in certain tests the tests results can be improved by modifying the centrifugation conditions. This applies especially to tests in which a matrix coated with a receptor, e.g. a second antibody, is used.

A preferred modification of the centrifugation conditions comprises an interval centrifugation i.e. a first centrifugation step then a pause and then a second centrifugation step. The centrifugation can optionally be carried out in several interval steps. The first centrifugation step is preferably only a short centrifugation step with a duration of up to 1 min, preferably up to 30 sec. Then there is a pause which can for example be 1 to 10 min or ca. 5 min. This is followed by a second centrifugation step of a longer duration and optionally also at a higher g number.

Certain aspects of the invention are elucidated in more detail by the following examples and figures.

BRIEF DESCRIPTION OF THE DRAWINGS

FIG. 3: shows the reactions that occur in a microreaction vessel in which the matrix contains anti-IgG antibodies:

a) in the reaction chamber and b) in the buffer supernatant of the matrix or in the matrix.

FIG. 4: shows a schematic result of a differential diagnosis of two different analytes (A1 and A2) in a reaction vessel:

a) patient sample 1, antibody positive for A1;

b) patient sample 2, antibody positive for A2;

c) sample 3 (mixture of sera from patients 1 and 2), antibody positive for A1 and A2;

d) patient sample 4, antibody negative for A1 and A2 and

EXAMPLES

1. Experiments with synthetic particles of the state of the art which do not function in the gel test (comparison)

Test procedure:

A suspension of commercially-available coloured synthetic particles which are usually present at concentrations of 10% solid particles (w/v) was washed with a 10 mM PBS solution pH 7.4 (Sigma P 4417), 0.1% Tween-20 (Sigma P 7949) (v/v) and adjusted to a concentration of 0.15% solid particles in the same solution.

25 $\mu$l of this suspension was pipetted in each case into a microreaction tube and sedimented under the conditions stated in table 1.

TABLE 1

Figure 1:
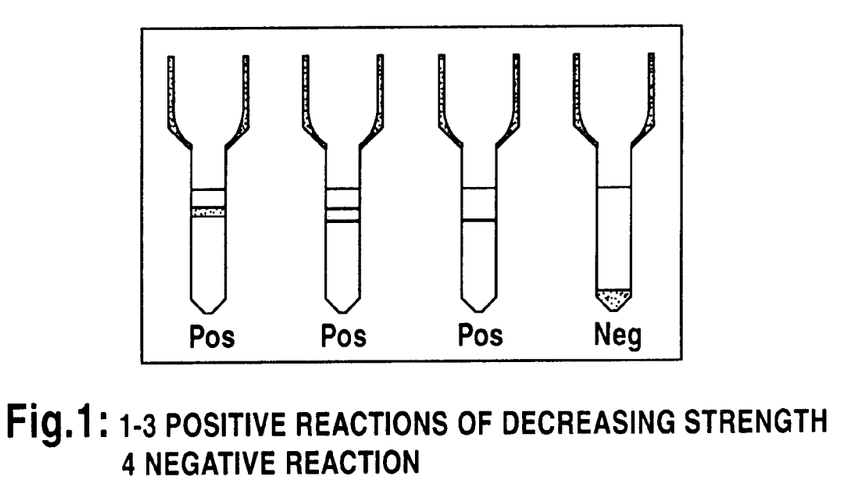
FIG. 1: shows the results that occur in the method according to the invention in the case of a positive, weak positive and negative reaction.
Figure 2:
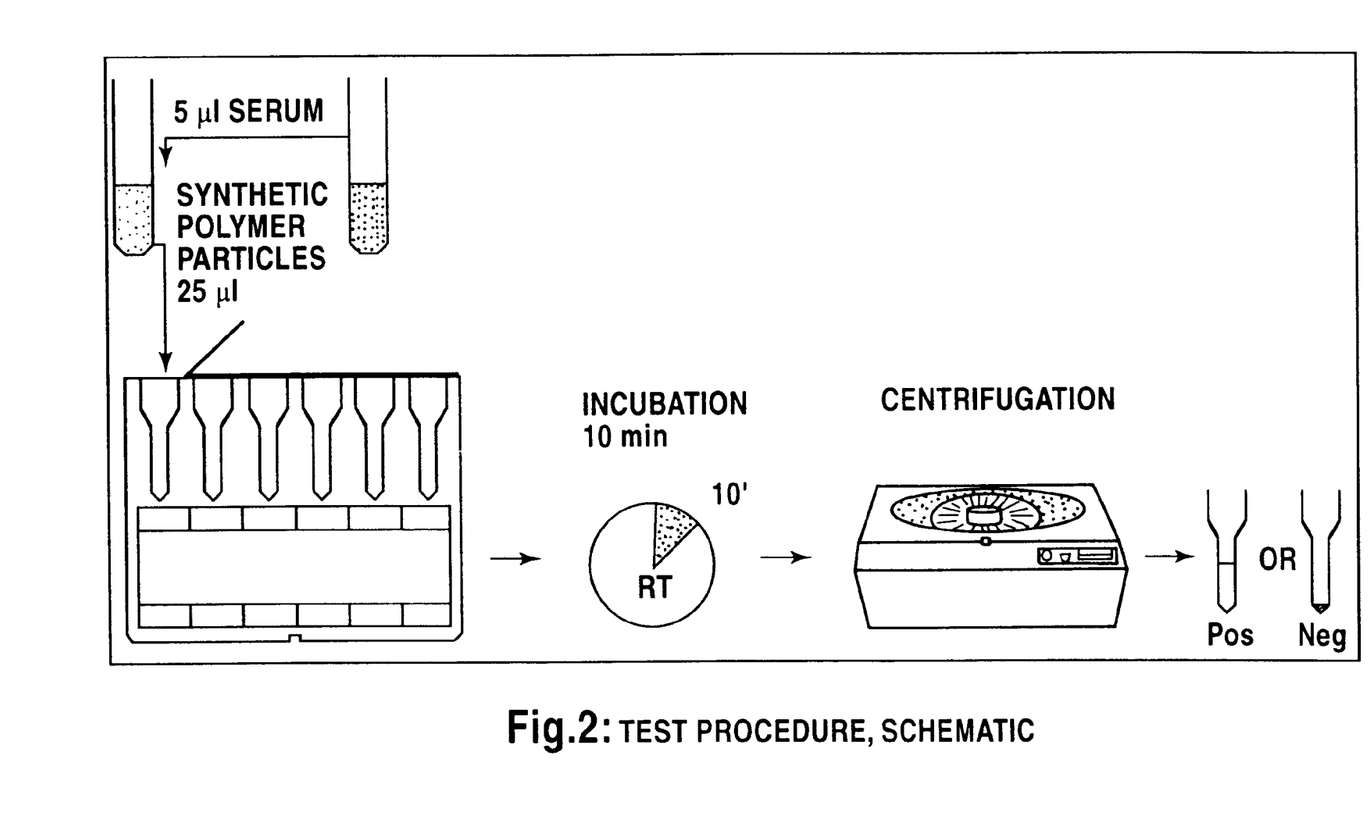
FIG. 2: shows a schematic representation of the test procedure
Figure 3:
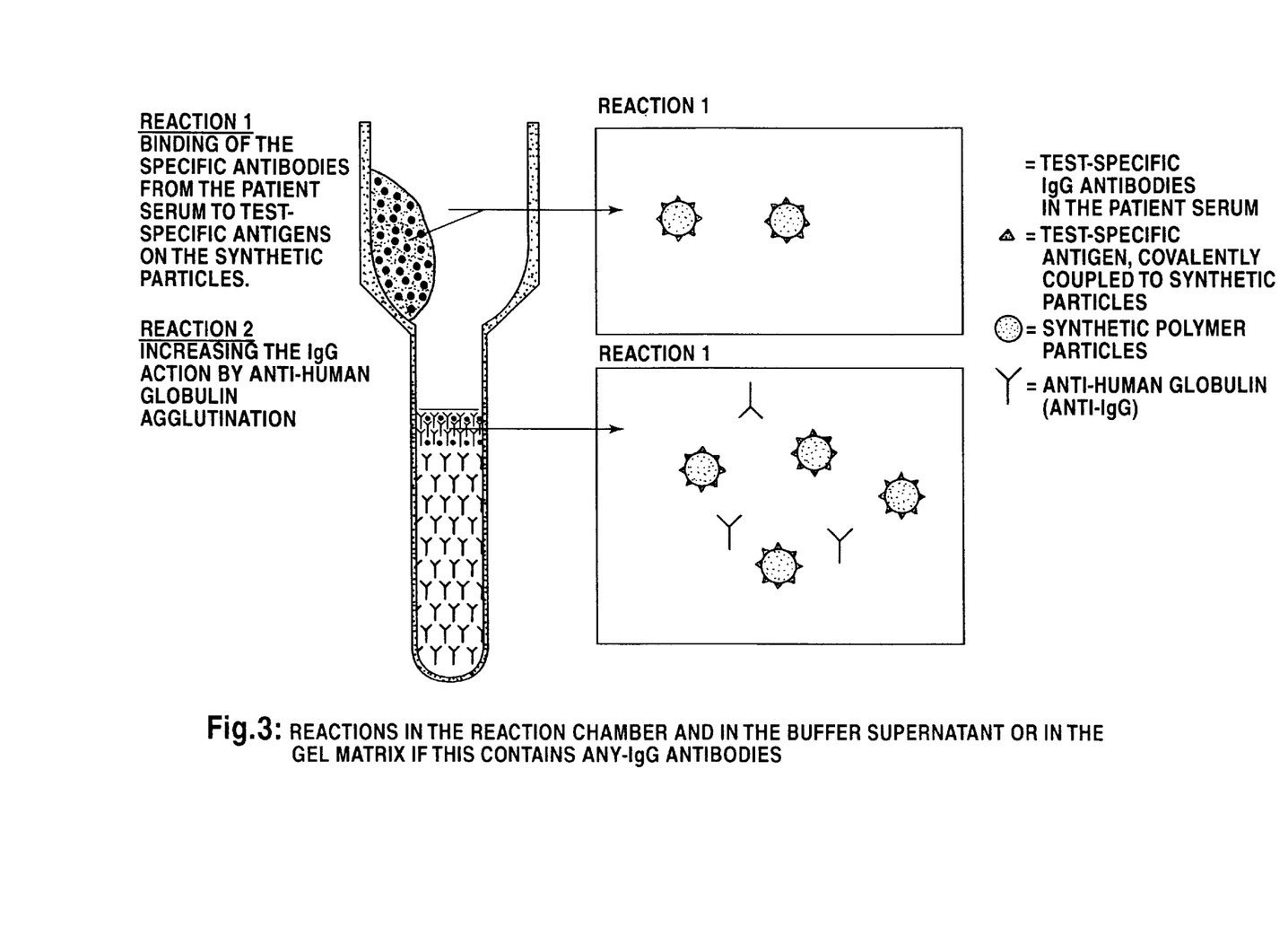
Figure 4:
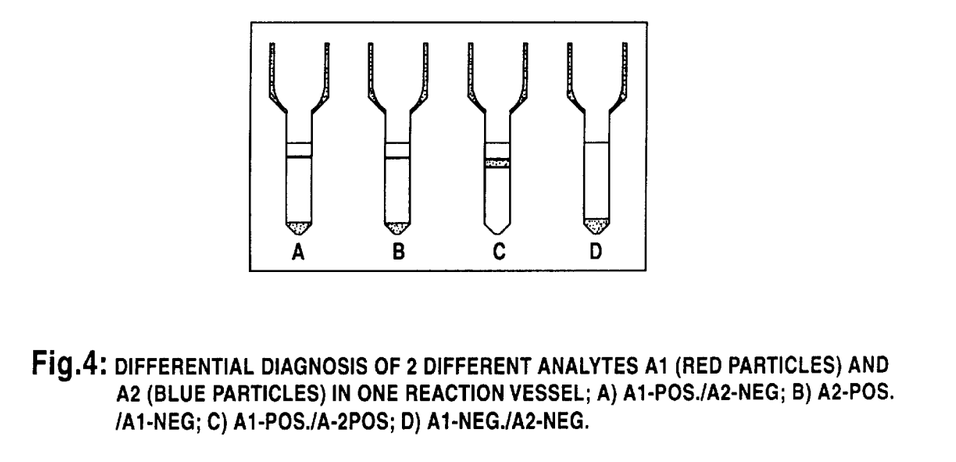
Figure 5:
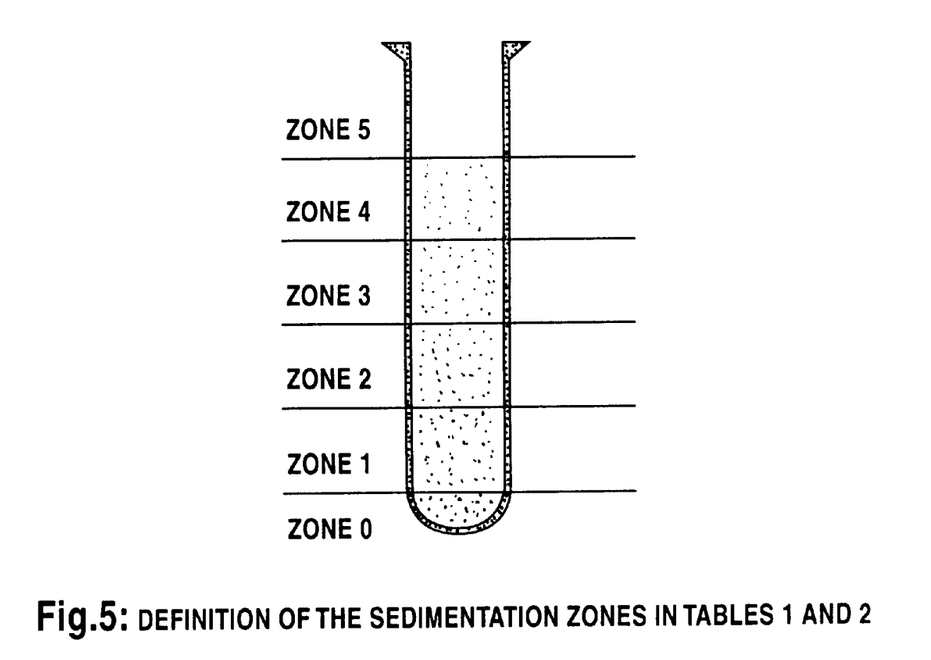
FIG. 5: shows a schematic representation of the reaction zones that are referred to in table 1. Zone 0 denotes: the particles form a sediment after centrifugation as is desirable for a negative reaction. Zone 5 means: no penetration of the gel matrix.

Properties of various commercially available synthetic particles and their sedimentation properties in a DiaMed ID system; zone definition according to FIG. 5.

Results:

| Batch No. | Colour | Diameter | Sedimentation behaviour in the gel | | | |
|---|---|---|---|---|---|---|
| | | | 10 min, 85 g | 20 min, 85 g | 40 min, 85 g | 50 min, 130 g |
| Polymer Laboratories, Churchstretton, UK: | | | | | | |
| Latex non-functionalized: | | | | | | |
| SP-1130 | blue | 0.10 $\mu$m | zone 4–5 | zone 4–5 | zone 3–4 | zone 3–4 |
| SP-1025 | red | 0.45 $\mu$m | zone 4–5 | zone 4–5 | zone 3–4 | zone 3–4 |
| SP-980 | red | 0.61 $\mu$m | zone 4–5 | zone 4–5 | zone 3–4 | zone 3 |
| SP-974 | red | 0.87 $\mu$m | zone 4–5 | zone 4–5 | zone 3 | zone 2–3 |
| Polymer Laboratories, Churchstretton, UK: | | | | | | |
| Microspheres non-functionalized: | | | | | | |
| SP-1016 | blue | 3.00 $\mu$m | zone 3–4 | zone 2–3 | zone 0–1 | zone 0–1 |
| SP-1269 | blue | 4.76 $\mu$m | zone 3–4 | zone 1–2 | zone 0–1 | zone 1 |
| SP-1024 | red | 11.9 $\mu$m | zone 4–5 | zone 4 | zone 4 | zone 4 |
| Molecular Probes: | | | | | | |
| Carboxylate FluoSpheres: | | | | | | |
| L-5191 | yellow-green | 0.01 $\mu$m | | zone 5 | | |
| L-5201 | yellow-green | 0.03 $\mu$m | | zone 5 | | |
| L-5221 | yellow-green | 0.10 $\mu$m | | zone 4–5 | | |
| L-5261 | yellow-green | 0.50 $\mu$m | | zone 4–5 | | |
| L-5281 | yellow-green | 1.00 $\mu$m | | zone 4–5 | | |
| L-5301 | yellow-green | 2.00 $\mu$m | | zone 3–4 | | |
| Sulphate fluospheres: | | | | | | |
| L-5121 | yellow-green | 4.00 $\mu$m | | zone 1–2 | | |
| Rhone Poulenc, Lyon, France: | | | | | | |
| Estapor: | | | | | | |
| K58 | green | 0.223 $\mu$m | | zone 4–5 | | |
| K80 | red | 0.299 $\mu$m | | zone 4–5 | | |
| Estapor, magnetic particles: | | | | | | |
| M180/12 | | 1.00 $\mu$m | | zone 2–4 | | |

2. Production of suitable synthetic particles

The synthetic particles used in the following examples were produced by dispersion polymerization since this method is in general the most suitable for producing particles in a range of 1 to 5 $\mu$m. In a first step base particles made of polystyrene were synthesized (2a). Subsequently the base particles were swollen to high density particles (2b) by a copolymerization with styrene/bromostyrene. In the following third step they were dyed (2c).

2a. Polymerization of the base particles

Procedure:

60 g 1-hexadecanol (Aldrich 25,874-1), 216 g polyvinylpyrrolidone 40,000 (PVP) (Aldrich 85,656-8), 1744 g dest. styrene (Aldrich S497-2) and 10261 g industrial methylated spirit (Banners IMS 99) were weighed into a 20 l round-bottom flask reactor (equipped with a stirrer, water condenser and nitrogen gassing). The stirrer speed was adjusted to 35–40 rpm. The mixture was gassed for 16 hours at room temperature. Subsequently the temperature was increased to 70° C. 17.4 g azo-bis-isobutyronitrile (Fisons A/9050/50) was then added to the reaction mixture upon which a white emulsion formed. After a further 24 hours the reaction mixture was cooled to room temperature. The resulting particles were washed by repeated centrifugation in methanol (3000 rpm, 5 min) and resuspended in a 0.1% (w/v) SDS (Fisons S/5200/53) solution after the last washing step. This preparation yielded 1573 g monodisperse polystyrene particles with a diameter of 2.3 μm.

2b. Production of high density particles
Procedure:

118.3 g of a 10% (w/v) suspension of 2.3 μm particles (produced according to example 2a) and 250 g of a polyvinyl alcohol (Harco 26-88) (PVA) (5% w/v) solution were weighed into a 1 l round-bottom flask reactor (equipped with a stirrer, water condenser and nitrogen gassing) and the stirrer speed was adjusted to 250 rpm. 1.5 g benzoylperoxide (Aldrich 22,887-7) was dissolved in 21.6 g 4-bromostyrene (Avocado 17896). This solution was emulsified in 250 ml of a 0.5% (w/v) SDS solution. The bromostyrene emulsion was then added to the round bottom flask reactor. After 3 hours 125 g of a 1% (w/v) sodium dichromate (Fisons S/3560/60) solution was added to the reactor and the temperature was increased to 70° C. After a further 16 hours the temperature was increased to 80° C. and reacted for a further 3 hours. Afterwards the reaction mixture was cooled to room temperature. The resulting particles were washed by repeated centrifugation in water and resulted in a yield of 26.98 g particles which now had a diameter of 3.1 μm. The nominal content of polymeric bromostyrene in these particles was 65% (w/v). The sedimentation rate of a 1% (w/v) suspension of these particles in water was 5.7 mm/hr, the theoretical density is 1.28 (see table 2).

Various particles of the same diameter but with different ratios of bromostyrene/styrene and thus of different levels of density were polymerized according to this process (table 2).

2c. Production of coloured high density particles
Procedure:
Sudan IV (red):

200 g of a 10% (w/v) suspension of synthetic high density particles (produced as described in 2a, 2b) with a diameter of 3.1 μm, 11.6 g of a 5% (w/v) solution polyvinyl alcohol (Harco 26-88), 40 g methanol (Hammond) and 240 g water were weighed into a 1 l round-bottom flask reactor (equipped with a PTFE stirrer, water condenser). 0.4 g of the dye Sudan IV (Kodak 112 6150) was dissolved in 30 g dichloromethane (Fisons D/1852/25) and the solution was emulsified in 250 ml of a 0.5% (w/v) SDS solution. The dichloromethane emulsion was then added to the rea ltor at room temperature. After 4 hours the resulting emulsion of red particles was added to a 2 l beaker. In order to evaporate the dichloromethane as rapidly as possible the surface of the suspension was gassed with nitrogen while stirring. The suspension was also gently heated to maximize the evaporation. The resulting red particles were washed by repeated centrifugation in water (1000 rpm, 5 min). They resulted in a yield of 19.8 g.

Ferro FW 1263 (blue):

50 g of a 10% (w/v) suspension of synthetic high density particles (produced as described in 2a, 2b) with a diameter of 3.1 μm, 2.9 g of a 5% (w/v) solution polyvinyl alcohol (Harco 26-88) and 60 g water were weighed into a 1 l round-bottom flask reactor (equipped with a PTFE stirrer, water condenser). 0.184 g of the dye Ferro FW1263 (Ferro Normandy Plastics Ltd, Westgate, Aldridge, GB) was dissolved in 7.5 g dichloromethane (Fisons D/1852/25) and this solution was emulsified in 62.5 ml of a 0.5% (w/v) SDS solution. The dichloromethane emulsion was then added to the reactor at room temperature. After 2 hours the resulting emulsion of blue particles was added to a 500 ml beaker. In order to evaporate the dichloromethane as rapidly as possible the surface of the suspension was gassed with nitrogen while stirring. The suspension was also gently heated to maximize the evaporation. The resulting blue particles were washed by repeated centrifugation in water (1000 rpm, 5 min). They resulted in a yield of 4.8 g.

3. Functionalization and streptavidin treatment of the particle surface
a) Production of aldehyde particles A 1 ml aliquot of red 3.1 μm high density particles (17.1%) (w/v) (produced as described in example 2a to 2c) was added to a 15 ml centrifuge tube and washed three times with ultrapure (18 megaohm) water by centrifugation (1000 rpm, 5 min). 15 ml of a solution of bovine serum albumin (2.67 mg/ml (Sigma A9647) in 10 mM PBS, pH 7.4, 0.05% NaN$_3$ was added to the particles washed in this manner and they were stirred for 4 hours at room temperature. The particles were washed 4 times with 15 ml water by centrifugation (1000 rpm, 5 min). Subsequently the particles were resuspended in 10 ml water in order to yield a concentration of 1.7% (w/v). 3.75 ml water was added to a 0.5 ml aliquot of this suspension to obtain a 0.2% (w/v) suspension. 4.25 ml of a 2% glutaraldehyde solution in water was added to this and the reaction mixture was stirred for 1 hour at room temperature. The particles were washed 4 times with 15 ml water by centrifugation (1000 rpm, 5 min).

b) Production of streptavidin particles

A suspension of 8 mg red 3.1 μm high density particles (produced as described in 2a–c and functionalized as described in 3a) was resuspended in 4 ml water and incubated for 1 min in an ultrasonic water-bath (Sonomatic from Langford Ultrasonics, Birmingham, GB). Subsequently 4 ml of a 50 mM sodium acetate buffer, pH 3.25 was added

TABLE 2

Sedimentation behaviour of synthetic particles with modified density using standard centrifugation conditions in a DiaMed ID system; zone definition according to FIG. 5.

| | | Particle | density | sedimentation behaviour in the gel | | |
|---|---|---|---|---|---|---|
| Styrene | Bromostyrene | diameter | [g/cm$^3$] | 5 min, 85 g | 10 min, 85 g | 20 min, 85 g |
| 100% | 0% | 3.1 μm | 1.05 | zone 4 | zone 3–4 | zone 2–3 |
| 64% | 36% | 3.1 μm | 1.18 | zone 0–1 | zone 0 | zone 0 |
| 35% | 65% | 3.1 μm | 1.28 | zone 0 | zone 0 | zone 0 |
| 23% | 77% | 3.1 μm | 1.32 | zone 0 | zone 0 | zone 0 | followed by 1 ml of an aqueous streptavidin solution (4 mg/ml). After a further 2 minutes in the ultrasonic waterbath 1 ml of a 50 mM sodium cyanoborohydride (Aldrich 15,615-9) solution in acetate buffer was immediately added. This mixture was incubated overnight at room temperature while shaking gently. The particles were washed 3 times with 15 ml water by centrifugation (1000 rpm, 5 min) and resuspended in 5.33 ml 10 mM PBS, pH 7.4 to adjust the particle concentration to 0.15% (w/v).

c) Production of polylysine particles 4 ml 50 mM Na-acetate, pH 3.25 was added to a suspension of 500 mg red 3.1 µm high density particles in 1 ml water (produced as described in 2a–c and functionalized as described in 3a). Then 4 ml of a 1 mg/ml poly-L-lysine (Sigma P 2636) solution in water was added. The reaction mixture was incubated for 4 min in an ultrasonic water-bath before adding 1 ml 50 mM sodium cyanoborohydride in acetate buffer. The reaction mixture was incubated overnight at room temperature while shaking gently. The particles were washed 3 times with water by centrifugation (1000 rpm, 5 min) and resuspended in 333 ml 10 mM PBS, pH 7.4 to adjust the particle concentration in the suspension to 0.15% (w/v).

4. Coupling of ligands to the functionalized particles a) High affinity binding 0.1 ml solutions of biotinylated antigens were added to 1 ml of a 0.15% (w/v) suspension red 3.1 µm high density particles (produced as in 2a–c, functionalized and treated with streptavidin as described in example 3a, 3b) in an Eppendorf microtube and incubated for 30 min while shaking. Unbound antigen was washed away by centrifuging twice (1000 rpm, 5 min) and resuspending in 1 ml of the above-mentioned buffer so that the final concentration of the particle suspension was again 0.15% (w/v).

b) Non-covalent coupling

10 µl of a 20 µ/ml ds DNA (Sigma D 1501) solution in 10 mM PBS pH 7.4 was added to 500 µl of a 0.15% suspension of red 3.1 µm high density polylysine particles (produced as described in 2a–c and 3a, 3c). After a vortex step (Bender & Hobein, Vortex Genie 2) for 5 sec at level 8, it was incubated for 12 hours at room temperature while gently shaking. The suspension was washed twice with 1 ml 10 mM PBS, pH 7.4 by centrifugation (1000 rpm, 5 min) and again resuspended in 500 µl 10 mM PBS, pH 7.4.

5. Buffer composition of the gel matrix

The gel matrix in the microreaction vessels was in the following aqueous buffer medium: 5 mM $KH_2PO_4$ (Merck 4873)/$Na_2HPO_4$ (Merck 6580), 150 mM NaCl (Fluka 71381), 0.024% (w/v) $NaN_3$ (Fluka 71290), 1.875% (v/v) albumin (Miles 81-177), 0.05% (w/v) EDTA (Fluka 03685), 1.3 mM Tris (Merck 8382), 1.25 mM N-acetyl-L-cysteine (Merck 12422), 0.025% (w/v) mucin (Sigma M 1778). Depending on the test, the gel matrix in addition optionally contained various amounts of anti-human globulin.

6. Chagas antibody test (high affinity binding of synthetic peptides)

a) Antigens

The synthetic peptides Ag-2, TcD and TcE are from Alta Bioscience (Birmingham, UK).

b) Coupling 1 ml aliquots of a 0.15% (w/v) suspension of red 3.1 µm high density particles (produced as described in 2a–c, functionalized and treated with streptavidin as described in examples 3a, 3b) were coupled to 2 ng TcD, 35 ng Ag-2 and 282 ng TcE which were synthesized by standard techniques and contained a biotinylated lysine in addition to the antigen sequence and were also purified over RP-HPLC by standard methods to >90% purity. For this purpose a 10× stock solution of the peptides in $H_2O$ (20 ng TcD, 350 ng Ag-2, 2820 ng TcE per ml) was prepared. For the coupling 1 vol. peptide solution was then added in each case to 10 vol. of a 0.15% (w/v) suspension of synthetic particles and rapidly mixed. The reaction mixture was then incubated for 30 min at room temperature while shaking gently. Subsequently the particle suspension was centrifuged for 5 min at 1000 rpm, the supernatant was decanted and washed twice with 10 mM PBS, pH 7.4. The final concentration of the particles in the suspension was again 0.15% (w/v). The particles sensitized in this manner were stored at 4° C.

c) Test procedure

A 0.15% (w/v) suspension of the synthetic particles sensitized as described in 4a was treated for 5 min in an ultrasonic water-bath. Then 25 µl in each case was added to a card containing 6 microtubes (see example 5: ID card, DiaMed, Cressier sur Morat) prefilled with a gel suspension containing an anti-human globulin (0.5%, v/v). Subsequently 1.5 µl patient serum or plasma was added. After 10 min incubation at room temperature they were centrifuged for 10 min at 85 g in a centrifuge specially developed for the microtubes (ID centrifuge 12 S II, DiaMed, Cressier sur Morat). The results can be evaluated immediately after the centrifugation.

d) Evaluation

Positive results are detectable as distinct bands on the gel or bands that have penetrated 1 to 2 mm into the gel. Even agglutinates distributed over the entire gel indicate positive reactions. Negative results are indicated by a distinct sediment of the synthetic particles sedimented to the bottom of the vessel, in this case there is no band in or on the gel.

7. Visceral Leishmaniasis antibody test (high affinity binding of recombinant antigen)

a) Antigens

Recombinant antigen rK39 from Corixa Inc., Seattle, USA.

b) Biotinylation and coupling 1 ml recombinant antigen rK39 (0.6 mg/ml) in 10 mM Tris, pH 8.0 was dialysed against 10 mM PBS, pH 7.4 (Sigma P 4417) at 4° C. and then filtered through a Puradisc 25 AS membrane filter (Whatman). The biotinylation was carried out with sulfo-NHS biotin (Pierce 21217). A 500 µl aliquot of rK39 in 10 mM PBS, pH 7.4 (300 µg) was added to 17.5 µl of an aqueous 1 mg/ml solution of sulfo-NHS biotin. The reaction mixture was incubated for 150 min at room temperature. The biotinylated rK39 was then separated from free biotin with a KwikSep desalting column (Pierce). The elution was carried out with 10 mM PBS, pH 7.4, 0.05% $NaN_3$.

1 ml aliquots of a 0.15% (w/v) suspension of red 3.1 µm high density particles (produced as described in 2a–2, functionalized and treated with streptavidin as described in examples 3a, 3b) were then coupled to 160 ng biotinylated rK39. For this a 10× stock solution was prepared in $H_2O$ (1600 ng rK39 per ml). The actual coupling was then carried out as described in example 6b.

c) Test procedure

The test procedure is identical to that of example 6 except that in the present case a suspension of synthetic particles is used which have been sensitized with rK39.

d) Evaluation: as in example 6

8. Hepatitis B surface antigen test (high affinity binding of monoclonal antibodies)

a) Antibody

The monoclonal antibody (MAb) MIH9701 directed towards the hepatitis B surface antigen detects both subtypes ad and ay and was obtained from Medix Biotech, Walchwil, Switzerland.

b) Biotinylation and coupling

200 μl of a 3 mg/ml solution MIH9701 was diluted to 1 ml with 0.1 M sodium acetate buffer, pH 5.5 and dialysed against the same buffer overnight at 4° C. 900 μl of an ice-cold 20 mM sodium metaperiodate solution in water was added to a 900 μl aliquot of the resulting MAb solution and the reaction mixture was incubated for 20 min at 0° C. in the dark. The reaction was stopped by addition of 11 μl of a 10% (w/v) glycerol solution. The MAb were separated from the other reaction components by a chromatographic step on a Kwiksep desalting column. The elution was carried out with 0.1 M acetate buffer, pH 5.5. The volume of the MAb after elution was 2.7 ml. 270 μl of a 50 mM solution of EZ-link biotin-LC-hydrazide (Pierce 21340) in dimethylsulfoxide (Sigma D 8418) was added to this and incubated for 2 hours at room temperature while shaking gently. The reaction mixture was then dialysed at 4° C. against 10 mM PBS, pH 7.4, 0.05% $NaN_3$ and subsequently filtered through a 0.2 μm Puradisc AS filter (Whatman). A subsequent desalting step again against 10 mM PBS, pH 7.4, 0.05% $NaN_3$ was carried out with a Kwiksep desalting column.

The MAb biotinylated in this manner were adjusted to 35 μg/ml in the same PBS buffer. Then 100 μl of the diluted MAb solution was added to 1 ml of a 0.15% (w/v) suspension of red 3.1 μm high density particles (prepared as described in 2a–c, functionalized and treated with streptavidin as described in 3a, 3b). This reaction mixture was incubated for 30 min at room temperature while gently shaking. The particles were then washed three times with the same buffer by centrifugation (1000 rpm, 5 min).

c) Test procedure

The test procedure was as in example 6 with the following differences:

i) A suspension of synthetic particles was used which were sensitized with MAb MIH9701.
ii) The gel matrix contained no anti-human globulins.

d) Evaluation: as in example 6

9. Test for anti-dsDNA antibodies (non-covalent binding of dsDNA)

a) Antigen double-stranded (ds)-DNA, type I obtained from Sigma (D-1501).

b) Coupling

10 μl of a 20 μg/ml dsDNA (Sigma D 1501) solution in 10 mM PBS, pH 7.4 was added to 500 μl of a 0.15% (w/v) suspension of red 3.1 μm high density particles (prepared as in 2a–c and 3a, 3c). After a vortex step (Bender & Hobein, Vortex Genie 2) for 5 sec at level 8 it was incubated for 12 hours at room temperature while shaking gently. The suspension was washed twice with 1 ml 10 mM PBS, pH 7.4 by centrifugation and resuspended in 500 μl 10 mM PBS, pH 7.4. The final concentration of the particles was again 0.15% (w/v), the sensitized particles were stored at 4° C.

c) Test procedure as in example 6 d) Evaluation: as in example 6.

10. HIV1/HIV2 antibody differentiation test (use of two species of synthetic particles sensitized in different ways with different colours but otherwise having the same physical properties)

a) Antigens

Synthetic peptide sequences from HIV-1 gp41 and HIV-2 gp36 from Alta Bioscience (Birmingham, UK).

b) Coupling as in example 6 with 72 ng gp-41 peptide and 40 ng gp36 peptide per 1 ml of a 0.15% (w/v) particle suspension. Red particles (produced as in 2a–c, functionalized and treated with streptavidin as described in example 3a, 3b) were sensitized with the HIV-2 specific peptide (antigen sequence from gp36) and blue particles (produced as in 2a–c, functionalized and treated with streptavidin as described in example 3a, 3b) were sensitized with the HIV-1 specific peptide (antigen sequence from gp41).

c) Test procedure

As in example 6 with the following differences: 10 μl in each case of a suspension of red and a suspension of blue particles was pipetted into the reaction chamber of a microtube. 2.5 μl patient serum was added to this.

d) Evaluation

HIV-1/HIV-2 positive results were detectable as distinct red/blue bands on the gel or bands that had penetrated 1 to 2 mm into the gel. In this case there was no sediment of particles. HIV-1 antibody positive results were indicated by a blue band on the gel or penetrated into the gel whereas the red particles formed a sediment on the bottom of the reaction vessel. HIV-2 antibody positive result were indicated by the opposite picture. HIV-1/HIV-2 negative results were seen as a distinct red/blue sediment on the bottom of the microreaction vessel.

11. Specific detection of non-IgM antibodies a) antigens

S. aureus protein A was from Sigma (P 6650); goat anti-human IgM antibody (μ chain specific)-biotin conjugate $F(ab)_2$ fragment was from Sigma (B 2641).

b) Biotinylation and coupling

The biotinylation of protein A was carried out as described in example 8. The biotinylated anti-IgM antibodies in 10 mM PBS, pH 7.4 were adjusted in one mixture to 40 μg/ml 3.1 μm high density particles (1.5%, w/v), in a further mixture to 1 μg/ml particles (0.15% w/v), the biotinylated protein A was adjusted to a concentration of 1 μg/ml particles (0.15% w/v). In this process 100 μl of 10-fold concentrated solutions in each case containing biotinylated anti-IgM antibodies (400 μg/ml or 10 μg/ml) or protein A (10 μg/ml) was added to 1 ml of a suspension of red 3.1 μm high density particles (prepared as described in 2a–c, functionalized and treated with streptavidin as described in 3a, 3b). This reaction mixture was incubated for 30 min at room temperature while shaking gently. The particles were then washed three times with the same buffer by centrifugation (1000 rpm, 5 min).

c) Test procedure 1 ml of the particles sensitized with anti-IgM was centrifuged for 5 min at 1000 rpm and the supernatant was discarded. 20 μl of a 1 to 10 dilution of the serum of a healthy person was added. After 5 sec vortex at level 8 the reaction mixture was incubated for 30 min at room temperature while shaking gently in order to adsorb the IgM antibodies of the serum. After a repeated centrifugation for 5 min at 1000 rpm the supernatant was removed. The following were pipetted into a card containing anti-IgG (as described in example 6):

position 1: 25 μl protein A particles (1 μg/ml)
position 2: 25 μl protein A particles (1 μg/ml)
position 3: 25 μl anti-IgM particles (1 μg/ml
position 4: 25 μl anti-IgM particles (1 μg/ml). 5 μl of the 1 to 10 diluted serum before adsorption was added to each position 1 and 3, and 5 μl of the 1 to 10 diluted serum after adsorption was added to each position 2 and 4. After 10 min incubation at room temperature it was centrifuged for 10 min at 85 g in a centrifuge specially developed for the microtubes (ID centrifuge 12 S II, DiaMed, Cressier sur Morat).

d) Evaluation

Both control tubes 1 and 3 exhibited distinct positive reactions as described in example 6. Of test mixtures 2 and 4, 2 exhibited a positive reaction which did not differ from that in tube 1 whereas at position 4 the particles formed a sediment on the bottom of the reaction vessel and thus indicated a negative reaction. This means that in this test it was possible to specifically detect a non-IgM antibody reaction.

12. Modified centrifugation for synthetic particles a) Antigens and coupling

The origin and coupling of the synthetic peptides are as in example 6.

b) Test procedure

Conventional

25 μl of the sensitized synthetic particles and then 5 μl serum/plasma were pipetted into the incubation chamber of prefabricated microtubes as described in example 6. After 10 min incubation at room temperature they were centrifuged for 10 min at 85 g in a centrifuge suitable for microtubes (ID centrifuge 12 S II, DiaMed, Cressier sur Morat).

Modified:

25 μl of the synthetic particles and afterwards 5 μl serum/plasma were pipetted into the incubation chamber of prefabricated microtubes as described in example 6. After 5 min incubation at room temperature the cards were placed in a modified ID centrifuge (DiaMed, Cressier sur Morat) with which the following special program was carried out:

1) 5 s centrifugation, 30 g
2) 5 min pause, 0 g
3) 10 min centrifugation, 85 g c) Evaluation The evaluation was carried out as in example 6. In tests which operated with gel matrices containing anti-IgG a general amplification especially of weak positive results is observed.

What is claimed is:

1. Method for the detection of an analyte in a sample liquid by agglutination, comprising the steps of:

contacting the sample liquid with an agglutination reagent in a reaction vessel that contains an inert matrix to form a reaction mixture, centrifuging the reaction mixture, and determining the reaction between the analyte and the agglutination reagent based on penetration of the agglutination reagent in the inert matrix, wherein the agglutination reagent comprises synthetic particles having an average diameter in the range of about 2–5 μm and a specific density of $\geq 1.1$, wherein the diameter and density are selected such that their sedimentation behavior towards the matrix is essentially the same as that of erythrocytes when the centrifugation is for 10 minutes at 85 g.

2. Method as claimed in claim 1, wherein the synthetic particles have a specific density in the range of 1.1–1.8.

3. Method as claimed in claim 2, wherein the synthetic particles have a specific density in the range of 1.15–1.4.

4. Method as claimed in claim 1, wherein the synthetic particles have a specific density in the range of 1.1–1.6.

5. Method as claimed in claim 1, wherein synthetic particles are used that are composed of organic polymers or copolymers.

6. Method as claimed in claim 5, wherein synthetic particles are used that are composed of styrene or styrene derivatives.

7. Method as claimed in claim 1, wherein dyed particles are used.

8. Method as claimed in claim 7, wherein particles coloured red are used.

9. Method as claimed in claim 1, wherein ligand molecules that are capable of binding to the analyte to be determined are immobilized on the surface of the particles.

10. Method as claimed in claim 9, wherein the ligand molecules are immobilized by adsorptive, covalent or high affinity interactions.

11. Method as claimed in claim 9, wherein peptides, proteins, nucleic acids, nucleic acid analogues, saccharides, lipids, hormones or metabolites are immobilized on the surface of the particles by covalent or high affinity interactions.

12. Method as claimed in claim 9, wherein cell membranes, fragments of cell membranes or lysates of cells or pathogens are bound to the surface of the particles by adsorptive interactions.

13. Method as claimed in claim 1, wherein the analyte is determined by an immune reaction.

14. Method as claimed in claim 13, wherein the analyte is an antibody.

15. Method as claimed in claim 14, wherein a class-specific detection of antibodies is carried out.

16. Method as claimed in claim 13, wherein the analyte is an antigen.

17. Method as claimed in claim 1, wherein the analyte is determined by a nucleic acid hybridization reaction.

18. Method as claimed in claim 1, wherein a particulate matrix is used.

19. Method as claimed in claim 18, wherein the average diameter of the matrix particles is in the range of 10–200 μm.

20. Method as claimed in claim 1, wherein several analytes are determined simultaneously using a differently coloured agglutination reagent for each analyte.

21. Method as claimed in claim 1, wherein the reaction mixture contains detergents or/and mucins.

22. Method as claimed in claim 1, wherein the reaction mixture contains a reducing agent.

23. Method as claimed in claim 1, wherein the centrifugation is carried out in several intervals.

24. Reagent kit for the detection of an analyte in a sample liquid comprising (a) at least one reaction vessel that contains an inert matrix and (b) at least one type of synthetic particles, said particles having an average diameter in the range of about 2–5 μm and a specific density of $\geq 1.1$, wherein the diameter and density are selected such that their sedimentation behavior towards the matrix is essentially the same as that of erythrocytes when the centrifugation is for 10 minutes at 85 g.

25. Reagent kit as claimed in claim 24, wherein several reaction vessels are arranged on a card or disk.

26. Reagent kit as claimed in claim 24, wherein the synthetic particles have a specific density in the range of 1.1–1.6.

* * * * *